United States Patent [19]

Maruyama et al.

[11] Patent Number: 5,028,467
[45] Date of Patent: Jul. 2, 1991

[54] DITHIOLATE METAL COMPLEX COMPOUND, PRODUCTION METHOD OF THE SAME, AND OPTICAL INFORMATION RECORDING MEDIUM COMPRISING THE SAME

[75] Inventors: Shoji Maruyama; Tsutomu Satoh, both of Yokohama; Kazukiyo Nagai, Numazu, all of Japan

[73] Assignee: Ricoh Company, Ltd., Tokyo, Japan

[21] Appl. No.: 397,731

[22] Filed: Aug. 23, 1989

Related U.S. Application Data

[63] Continuation-in-part of Ser. No. 381,576, Jul. 18, 1989, abandoned.

[30] Foreign Application Priority Data

Aug. 23, 1989 [JP] Japan ................. 63-209760

[51] Int. Cl.$^5$ ............................................. B32B 3/02
[52] U.S. Cl. ........................................ 428/64; 428/65; 428/195; 428/913; 430/945; 346/76 L; 346/135.1; 369/275.1; 369/288
[58] Field of Search ............... 369/275, 288; 430/945, 430/270, 495; 346/76 L, 135.1; 428/195, 64, 65, 913

[56] References Cited

U.S. PATENT DOCUMENTS

| | | | |
|---|---|---|---|
| 4,707,425 | 11/1987 | Sasagawa et al. | 430/21 |
| 4,832,992 | 5/1989 | Yabe et al. | 427/384 |
| 4,860,273 | 8/1989 | Sawano et al. | 369/100 |

FOREIGN PATENT DOCUMENTS

| | | | |
|---|---|---|---|
| 196180 | 8/1989 | Japan | . |
| 2222162 | 2/1990 | United Kingdom | . |

*Primary Examiner*—Patrick J. Ryan
*Attorney, Agent, or Firm*—Cooper & Dunham

[57] ABSTRACT

A dithiolate metal complex compound having formula [I]

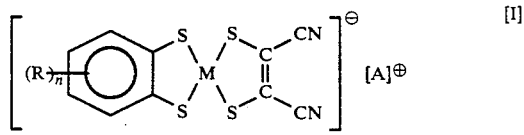

wherein each R individually represents an alkyl group having 1 to 6 carbon atoms, a halogen, a halogenated alkyl group having 1 to 6 carbon atoms, an amino group which may be substituted with 1 or 2 alkyl groups each having independently 1 to 4 carbon atoms, or a trifluoromethyl group, M represents a transition metal selected from the group consisting of Ni, Pd, Pt, Co, Cu and Mn, n is an integer of 0 to 4, and A represents the counter cation of the complex compound, a method of producing the same, and an optical information recording medium comprising a recording layer comprising a polymethine dye and the dithiolate metal complex compound are disclosed.

40 Claims, 6 Drawing Sheets

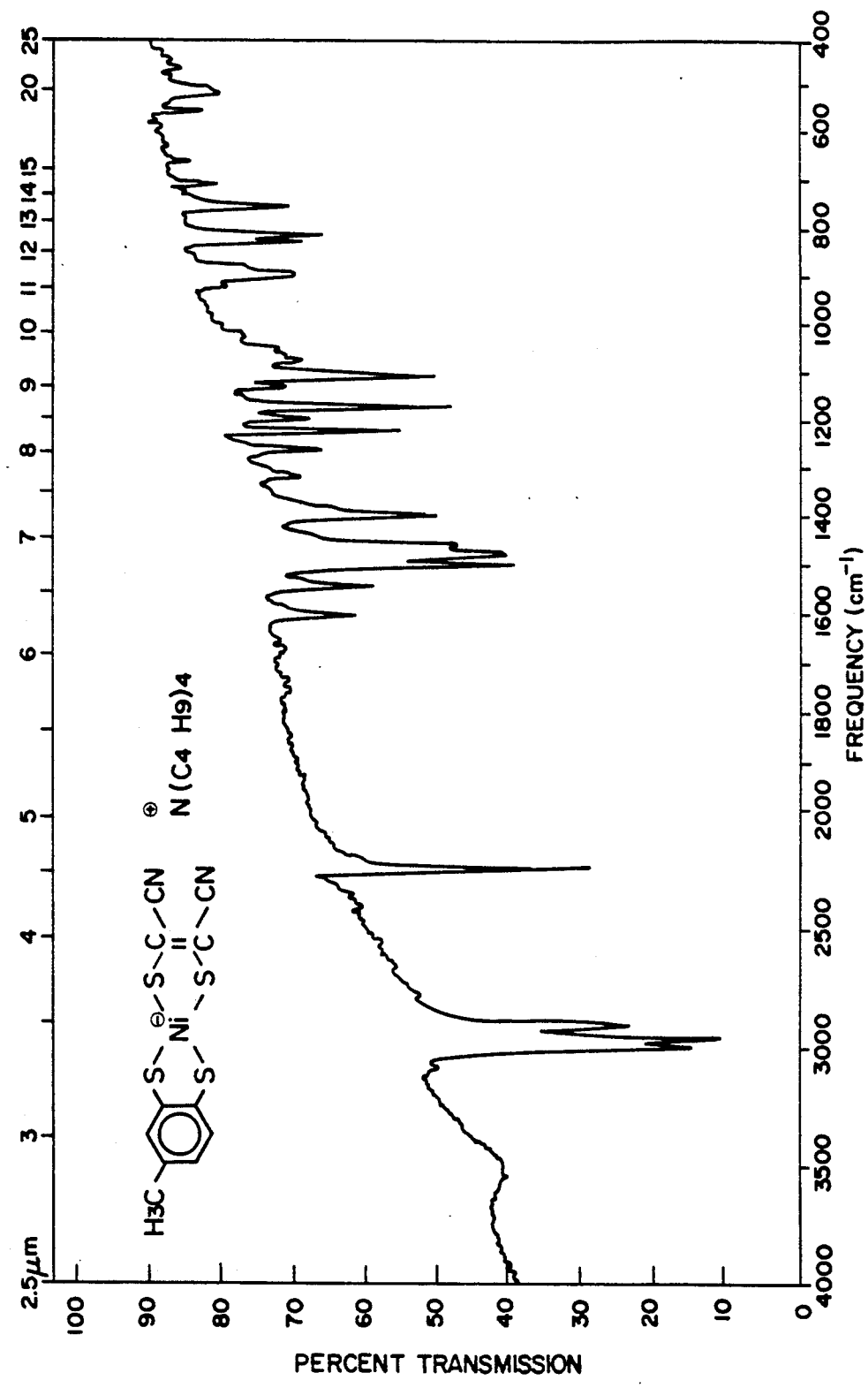

F I G. 2-2
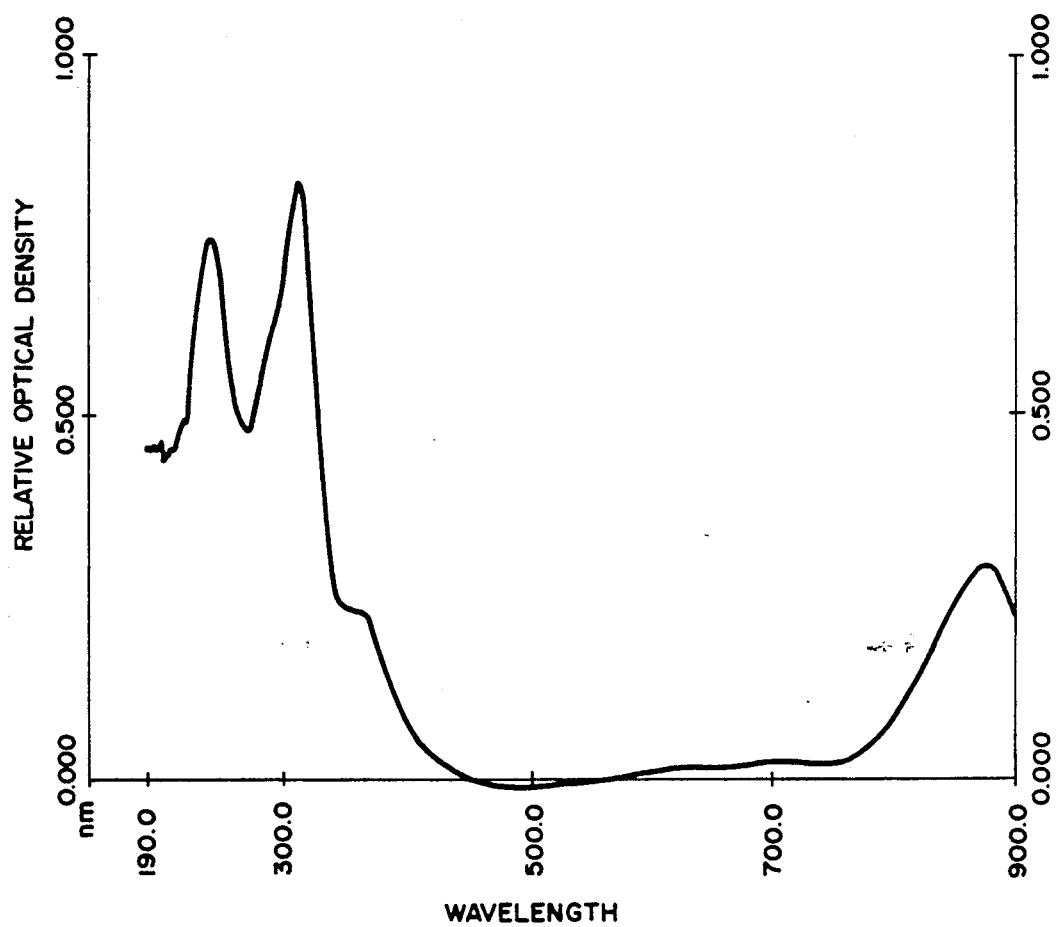

DITHIOLATE METAL COMPLEX COMPOUND, PRODUCTION METHOD OF THE SAME, AND OPTICAL INFORMATION RECORDING MEDIUM COMPRISING THE SAME

CROSS-REFERENCE TO RELATED APPLICATION

This application is a continuation-in-part of applicants' copending U.S. patent application Ser. No. 381,576, filed July 18, 1989 now abandoned.

BACKGROUND OF THE INVENTION

1. Field of the Invention

This invention relates to a dithiolate metal complex compound usable as a dye component in an optical information recording medium, a production method of the complex compound, and an optical information recording medium comprising a polymethine dye and the complex compound.

2. Discussion of Background

Recently, a thin film containing as its main component an organic dye having both light-absorptivity and light-reflectivity, such as a cyanine dye, a triaryl methane dye, a mercocyanine dye, a naphthoquinone dye, a xanthene dye or a squalyrium dye, has been proposed as a recording layer for use in an optical information recording medium, for example, in Japanese Laid-Open Patent Applications 51-135886, 57-11090 and 61-70503.

The conventional recording layer made of a metallic thin film is now being substituted by a recording layer made of the above organic thin film. A thin film containing the organic dye has a low melting point and decomposition point, and also has low thermal conductivity, so that a recording layer made of such an organic thin film has high sensitivity, allowing information to be recorded in this layer with high density.

In addition to the above-mentioned advantages, the thin film containing the organic dye can be simply formed by a coating method, so that it can be produced with higher productivity and lower production cost.

The thin film containing the organic dye, however, cannot stand for a long term because the organic dye tends to lose its color when natural light or a reproduction laser beam is repeatedly applied to the film. Moreover, when the thin film is formed by a coating method, a halogenated hydrocarbon or the like is used as a solvent, so that limitations are placed on resins which can be used as a substrate.

In order to overcome the above shortcomings, intensive studies are now being carried out both on dyes which are highly stable in natural light in the red to near-infrared region, as well as in a reproduction light, and on stabilizing agents which will effectively improve the stability in the light.

SUMMARY OF THE INVENTION

Accordingly, an object of this invention is to provide a dithiolate metal complex compound, usable in a recording layer of an optical information recording medium, free from the above shortcomings of the conventional organic dyes.

Another object of this invention is to provide a production method of the dithiolate metal complex compound.

A further object of this invention is to provide an optical information recording medium comprising the dithiolate metal complex compound, which is highly stable in natural light and a reproduction light.

The first object of the present invention can be attained by a dithiolate metal complex compound consisting of an anion and a counter cation, having formula [I]:

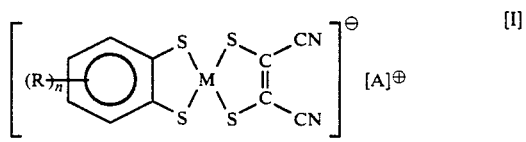

wherein
each R individually represents an alkyl group having 1 to 6 carbon atoms, a halogen, a halogenated alkyl group having 1 to 6 carbon atoms, an amino group which may be substituted with 1 or 2 alkyl groups each having independently 1 to 4 carbon atoms, or a trifluoromethyl group, M represents a transition metal selected from the group consisting of Ni, Pd, Pt, Co, Cu and Mn, n is an integer of 0 to 4, and A represents the counter cation of the complex compound.

Preferably, the counterion A is a quaternary ammonium or phosphonium cation; more particularly, it may be a cation of the general formula:

$$MR_4^+$$

wherein
M is nitrogen or phosphorus
and R each individually is alkyl of 1 to 20 carbon atoms, or arylalkyl, wherein aryl has 6 to 10 carbon atoms and wherein alkyl has 1 to 6 carbon atoms, or, if M is nitrogen, three R's are taken together to form a double bond and part of a nitrogen containing aromatic ring system of 5 to 9 carbon atoms and 1 to 3 nitrogen atoms which may be substituted with 1 to 4 alkyl of 1 to 4 carbon atoms.

"Alkyl" refers to a straight or branched saturated hydrocarbyl group having from 1 to 20 carbon atoms. Specific examples are methyl, ethyl, propyl, isopropyl, n-butyl, isobutyl, sec-butyl, tert-butyl, pentyl, 2- and 3-methylbutyl, 2,2-dimethylbutyl, hexyl, heptyl, octyl, nonyl, decyl, undecyl, lauryl, pentadecyl, palmityl and stearyl.

Aryl having 6 to 10 carbon atoms is for example phenyl, 1-naphthyl and 2-naphthyl.

Arylalkyl comprises an alkyl group as defined above having 1 to 6 carbon atoms and having as substituent an aryl as defined above.

Nitrogen containing aromatic ring systems having 5 to 9 carbon atoms and 1 to 3 nitrogen atoms are for example pyridine, picoline, pyrimidine, quinoline, isoquinoline and 1, 8-naphthyridine.

Halogen is preferably fluorine, chlorine or bromine.

The second object of the present invention can be attained by a production method of the dithiolate metal complex compound consisting of an anion and a counter cation having formula [I], comprising the step of reacting (a) a neutral dithiolate metal complex having formula [II] or onium salt of the mono-anion thereof:

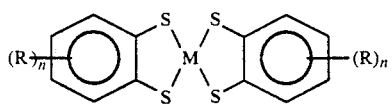

wherein each R individually represents an alkyl group having 1 to 6 carbon atoms, a halogen, a halogenated alkyl group having 1 to 6 carbon atoms, an amino group which may be substituted with 1 or 2 alkyl groups each having independently 1 to 4 carbon atoms, or a trifluoromethyl group,.

M represents a transition metal selected from the group consisting of Ni, Pd, Pt, Co, Cu and Mn, and n is an integer of 0 to 4, with (b) a bis-(onium) salt of dicyanoethylenedithiolate metal complex having formula [III]:

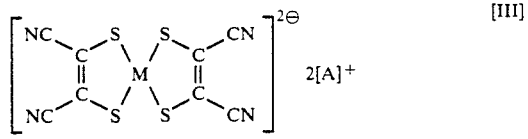

wherein

M represents a transition metal selected from the group consisting of Ni, Pd, Pt, Co, Cu and Mn, and A represents the counter cation of the complex compound.

The third object of the present invention can be attained by an optical information recording medium comprising a substrate and a recording layer formed on the substrate, comprising a polymethine dye and the dithiolate metal complex compound having formula [I']:

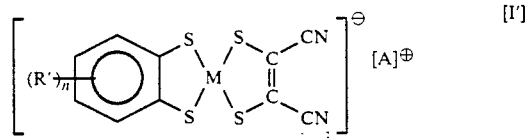

wherein each R' individually represents an alkyl group having 1 to 6 carbon atoms, a halogen, a halogenated alkyl group having 1 to 6 carbon atoms, an amino group which may be substituted with 1 or 2 alkyl groups each having independently 1 to 4 carbon atoms, a trifluoromethyl group, a cyano group, or a nitro group, M represents a transition metal selected from the group consisting of Ni, Pd, Pt, Co, Cu and Mn, n is an integer of 0 to 4, and A represents the counter cation of the complex compound.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1—1 is a chart showing the infrared spectrum of the metal complex compound according to the present invention prepared in Example 1;

FIG. 1-2 is a chart showing the absorption curve of the metal complex compound according to the present invention prepared in Example 1;

FIG. 2-1 is a chart showing the infrared spectrum of the metal complex compound according to the present invention prepared in Example 2;

FIG. 2—2 is a chart showing the absorption curve of the metal complex compound according to the present invention prepared in Example 2;

FIG. 3-1 is a chart showing the infrared spectrum of the metal complex compound according to the present invention prepared in Example 3; and FIG. 3-2 is a chart showing the absorption curve of the metal complex compound according to the present invention prepared in Example 3.

DETAILED DESCRIPTION OF THE PREFERRED EMBODIMENTS

Figures 1, 2:
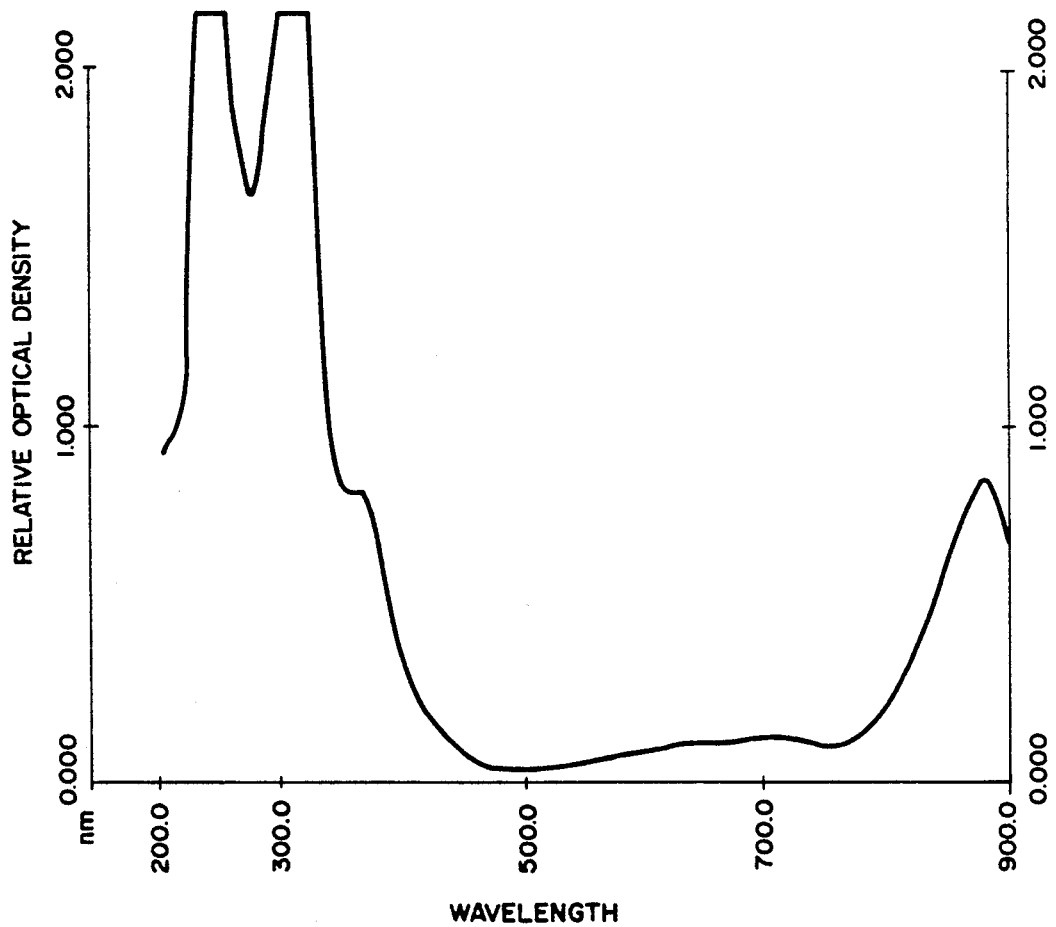
Figures 1, 2:
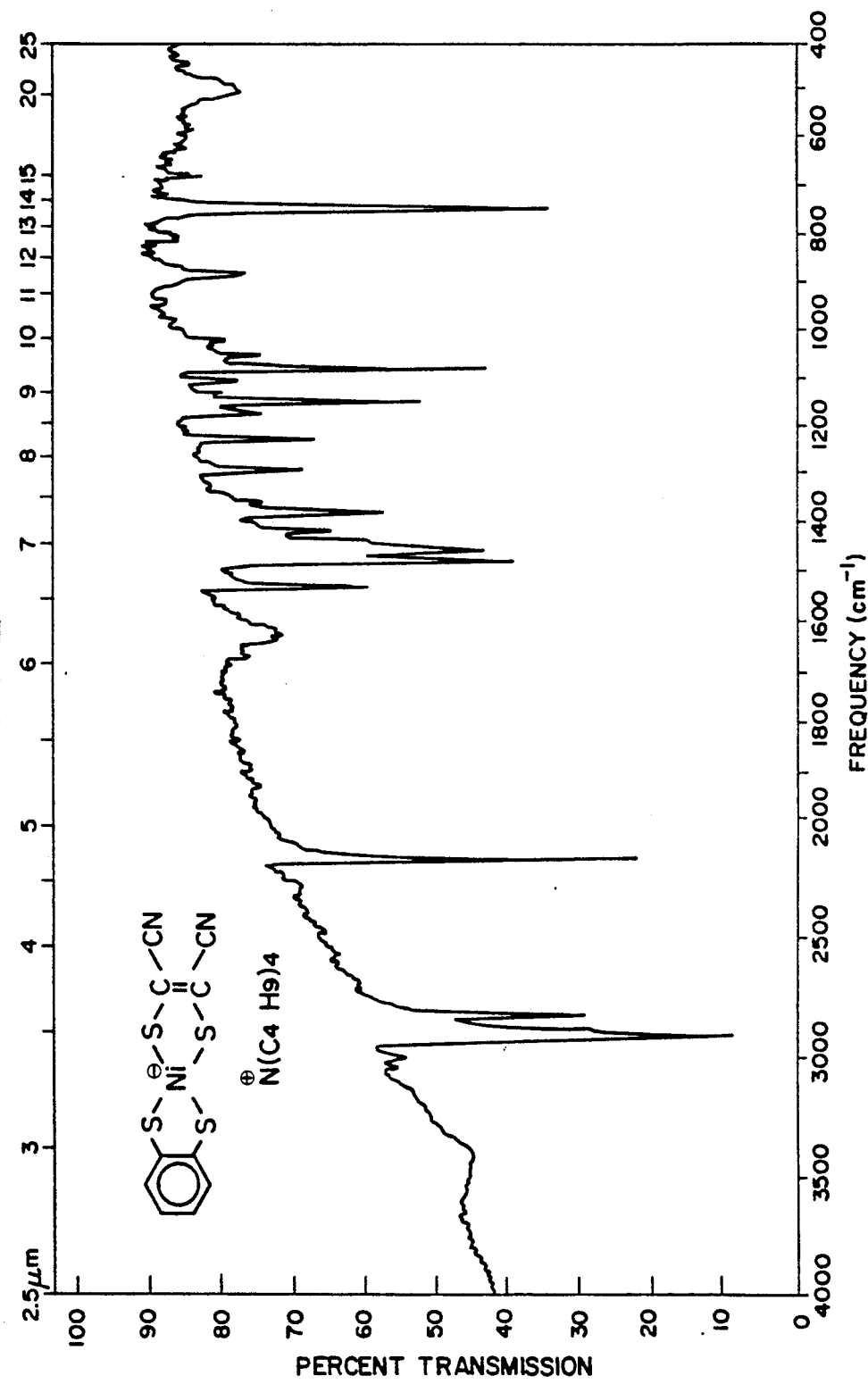

The dithiolate metal complex compound according to the present invention having formula [I] is a compound of a benzenedithiolate—dicyanoethylenedithiolate metal complex anion and its counter cation represented by A in formula [I]. Since the dithiolate metal complex compound has an absorptivity in the near-infrared region, it is quite useful in an optical recording medium.

Examples of the metal complex compounds having formula [I] according to the present invention include those compounds which can be prepared by combining the following complex anions with the following complex cations; however, this invention is not restricted by these compounds.

(1) Examples of Complex Anions 1. (1,2-benzenedithiolate)-(1,2-dicyano-1,2-ethylenedithiolate)Ni(III)

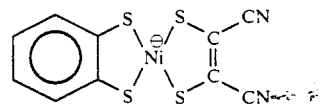

2. (1-methyl-3,4-benzenedithiolate)-(1,2-dicyano-1,2-ethylenedithiolate)Ni(III)

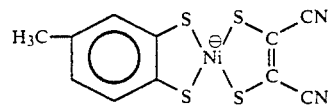

3. (1,4-dimethyl-2,3-benzenedithiolate)-(1,2-dicyano-1,2-ethylenedithiolate)Ni(III)

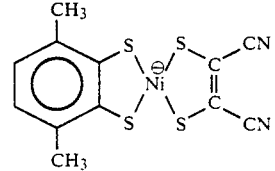

4. (1,2,3,4-tetramethyl-5,6-benzenedithiolate)-(1,2-dicyano-1,2-ethylenedithiolate)Ni(III)

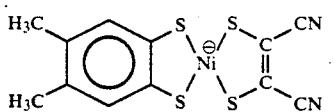

5. (1-t-butyl-3,4-benzenedithiolate)-(1,2-dicyano-1,2-ethylenedithiolate)Ni(III)

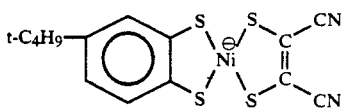

6. (1-dimethylamino-3,4-benzenedithiolate)-(1,2-dicyano-1,2-ethylenedithiolate)Ni(III)

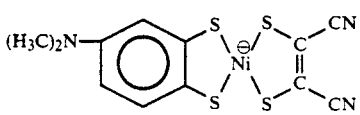

7. (1-fluoro-2,3-benzenedithiolate)-(1,2-dicyano-1,2-ethylenedithiolate)Ni(III)

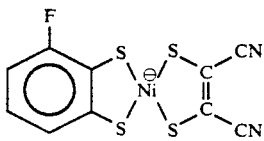

8. (1-chloro-2,3-benzenedithiolate)-(1,2-dicyano-1,2-ethylenedithiolate)Ni(III)

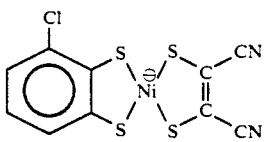

9. (1,4-dichloro-5,6-benzenedithiolate)-(1,2-dicyano-1,2-ethylenedithiolate)Ni(III)

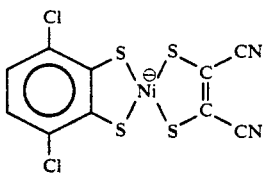

10. (1,2,4-trichloro-5,6-benzenedithiolate)-(1,2-dicyano-1,2-ethylenedithiolate)Ni(III)

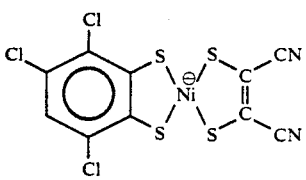

11. (1,2,3,4-tetrachloro-5,6-benzenedithiolate)-(1,2-dicyano-1,2-ethylenedithiolate)Ni(III)

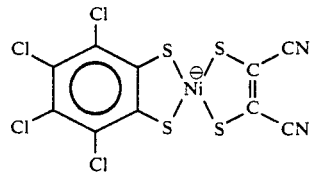

12. (1-bromo-2,3-benzenedithiolate)-(1,2-dicyano-1,2-ethylenedithiolate)Ni(III)

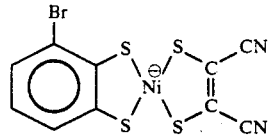

13. (1,2,3,4-tetrabromo-5,6-benzenedithiolate)-(1,2-dicyano-1,2-ethylenedithiolate)Ni(III)

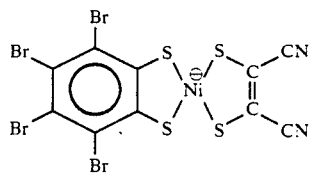

14. (1-trifluoromethyl-3,4-benzenedithiolate)-(1,2-dicyano-1,2-ethylenedithoilate)Ni(III)

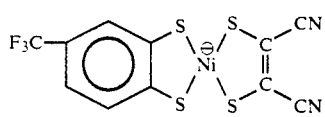

In the optical information recording medium of the present invention, the following complex anions can also be employed:

(1-cyano-3,4-benzenedithiolate)-(1,2-dicyano-1,2-ethylenedithiolate)Ni(III)

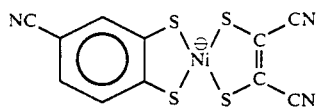

(1-nitro-2,3-benzenedithiolate)-(1,2-dicyano-1,2-ethylenedithiolate)Ni(III)

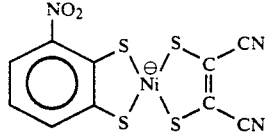

The above compound can be prepared by the steps of synthesizing 3,4-dithiolate-1-benzonitrile in accordance with a process shown in Japanese Laid-Open Patent Application 58-105960, using 3,4-dichloro-1-benzonitrile as a starting material, obtaining the corresponding complex of formula [II], and conducting a ligand exchanging reaction of the complex with a dicyanoethylenedithiolate metal complex onium salt of formula [III].

In the above examples of complex anions, Ni can be replaced by Pd, Pt, Co, Cu or Mn.

(2) Examples of Complex Cations (Counter Cations A)

1. tetraethylammonium cation

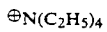

2. tetra-n-butylammonium cation

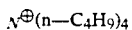

3. benzyl-tributylammonium cation

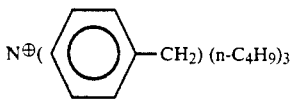

4. N-laurylpyrridinium cation

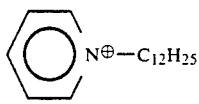

5. N-benzylpicolinium cation

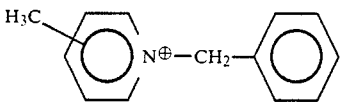

6. trimethyl-hexadecaneammonium cation

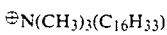

7. tetra-n-butylphosphonium cation

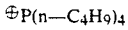

8. trihexylethylphosphonium cation

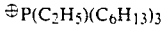

9. tetraoctylphosphonium cation

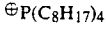

The metal complex compound having formula [I] according to the present invention is readily obtainable by reacting (a) a neutral dithiolate metal complex having formula [II] or onium salt of the mono-anion thereof:

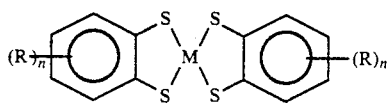

wherein
each R individually represents an alkyl group having 1 to 6 carbon atoms, a halogen, a halogenated alkyl group having 1 to 6 carbon atoms, an amino group which may be substituted with 1 or 2 alkyl groups each having independently 1 to 4 carbon atoms, or a trifluoromethyl group, M represents a transition metal selected from the group consisting of Ni, Pd, Pt, Co, Cu and Mn, and n is an integer of 0 to 4, (b) with a bis-(onium) salt of a dicyanoethylenedithiolate metal complex having formula [III]:

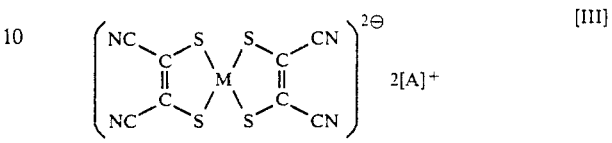

wherein
M represents a transition metal selected from the group consisting of Ni, Pd, Pt, Co, Cu, and Mn,
and A represents the counter cation of the complex compound.

Namely, in order to obtain the metal complex compound of the present invention having formula [I], it is preferable to utilize a ligand exchange reaction between the dithiolate metal complex having formula [II] and the onium salt of dicyanoethylenedithiolate metal complex having formula [III].

For example, the following compound,

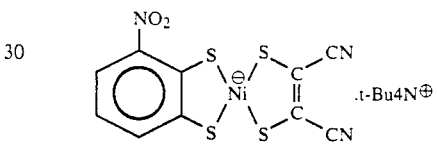

can be prepared by the steps of synthesizing 1-nitrobenzene-2,3-dithiolate in accordance with a process shown in Japanese Laid-Open Patent Application 58-105960, using 2-3-dichloronitrobenzene as a starting material, obtaining the corresponding complex of formula [II], and conducting a ligand exchanging reaction of the complex with a dicyanoethylenedithiolate metal complex onium salt of formula [III].

Note that preferable examples of the halogen indicated by R in the above formulae [I] and [II] and fluorine, chlorine and bromine.

The above reaction between the dithiolate metal complex [II] and the onium salt of the metal complex [III] proceeds in an organic solvent, and it is preferable to reflux the reaction system while the reaction progresses. As the organic solvent, acetone, acetonitrile, 1,2-dichloroethane and dimethylsulfoxide in which the metal complexes formulae [II] and [III] can be dissolved are preferably employed.

It is preferable to react the metal complex [II] with the onium salt of the metal complex [III] in a molar ratio ranging from 1:1 to 1:1.2. These two metal complexes are dissolved in any of the above-described solvents, and the reaction system is heated to the reflux temperature of the solvent or a temperature between 80° and 90° C. in order to initiate the reaction between the two metal complexes. The reaction time can range from 0.5 to 6 hours, preferably 2 to 4 hours.

The dithiolate metal complex having formula [II] can be prepared by reacting a disodium salt of benzenedithiols with a transition metal compound such as nickel chloride as described in "JACS", 88, 43 (1966) by Raymond Williams, et al. The onium salt of bis(substituted or unsubstituted benzenedithiolate) metal complex can be prepared by adding a quaternary ammonium or phosphonium compound to the above reaction mixture. It is preferable to dissolve the thus prepared onium salt of the dithiolate metal complex in an aprotic polar solvent like acetonitrile, and form the neutral complex by using an oxidizing agent such as iodine prior to subject it to a ligand exchange reaction.

The bis-(onium) salt of dicyanoethylenedithiolate metal complex [III] can be prepared in the following manner. Namely, sodium cis-1,2-dicyano-1,2-ethylenedithiolate is synthesized by using sodium cyanate, carbon disulfide and dimethylformamide in the manner described in "Inorganic Synthesis", 10, 8(1967). The synthesized compound is reacted with a transition metal compound such as nickel chloride according to the method described in E. Billig, R. Williams, I. Bernal and H. B. Gray, Inorg. Chem. 3, 663–6 (1964). Thereafter, a quaternary ammonium or phosphonium compound is added to the reaction mixture to obtain the desired bis(onium) salt of bis(cis-1,2-dicyano-1,2-ethylenedithiolate) metal complex.

A recording layer prepared by incorporating the dithiolate metal complex compound having formula [I] into an organic thin film containing as the main component a polymethine dye is employed in the optical information recording medium according to the present invention. The recording medium has high resistance to natural light and reproduction light, so that it is stable and preservable for a long term.

The basic structure of the optical information recording medium of the present invention is such that the recording layer comprising the polymethine dye and the metal complex compound having the following formula [I'] is directly formed on a substrate:

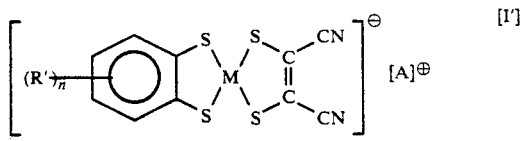

wherein
each R' individually represents an alkyl group having 1 to 6 carbon atoms, a halogen, a halogenated alkyl group having 1 to 6 carbon atoms, an amino group which may be substituted with 1 or 2 alkyl groups each having independently 1 to 4 carbon atoms, a trifluoromethyl group, a cyano group, or a nitro group,
M represents a transition metal selected from the group consisting of Ni, Pd, Pt, Co, Cu and Mn,
n is an integer of 0 to 4,
and A represents the counter cation of the complex compound. However, an undercoat layer may be interposed between the substrate and the recording layer, and a protective layer may be provided on the recording layer, if necessary. A pair of the thus prepared recording media can be fabricated into an "air-sandwiched" structure with the recording layers facing each other, or the two recording media can be sticked together, facing each other with a protective layer.

Note that preferable examples of the halogen indicated by R in the above formula [I'] are fluorine, chlorine and bromine.

Examples of the polymethine dye to be used, as the main component, in the recording layer of the present invention include cyanine dyes, merocyanine dyes, croconium dyes, pyrylium dyes, azulenium dyes and squalyrium dyes. Of these, cyanine dyes and merocyanine dyes are preferable; and cyanine dyes having formulae [IV] and [V], and merocyanine dyes having formula [VI] are preferably employed.

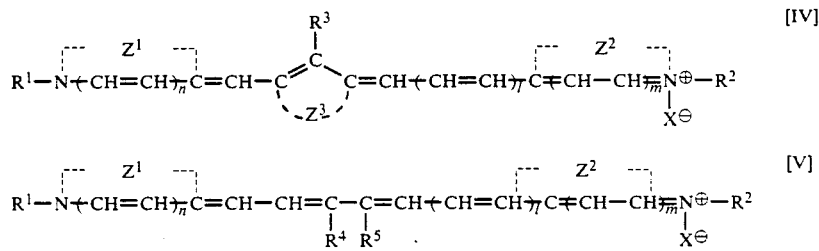

wherein
$R^1$ and $R^2$ each represent a substituted or unsubstituted alkyl group, a substituted or unsubstituted arylalkyl group, or an alkenyl group,
$Z^1$ and $Z^2$ each represent an atomic group necessary for forming a substituted or unsubstituted heterocyclic ring for example, indole, thiazole, oxazole, pyrrol, selenazole, quinolinium, benzthiazole, and benzoselenazole rings.
$Z^3$ represents an atomic group necessary for forming a substituted or unsubstituted penta- or hexa-cyclic ring, the penta- or hexa-cyclic ring may be condensed with an aromatic ring for example,

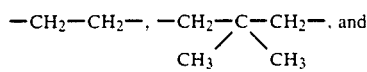

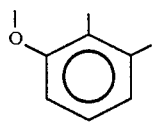

$R^3$ represents a hydrogen atom or a halogen,
$R^4$ and $R^5$ each represent a hydrogen atom, a halogen, a hydroxyl group, a carboxyl group, an alkyl group, a substituted or unsubstituted aryl group, or an acyloxyl group, $X^-$ represents an acidic anion, and l, m and n are 0 or 1.

(Merocyanine Dyes)

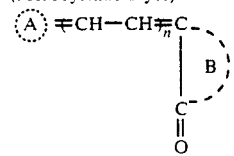

-continued
wherein 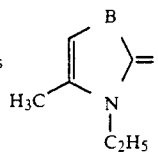 represents a ring such as
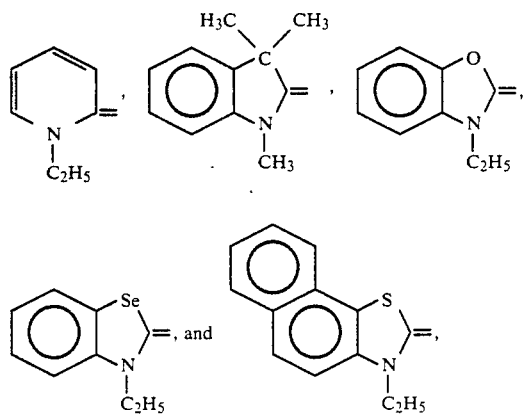
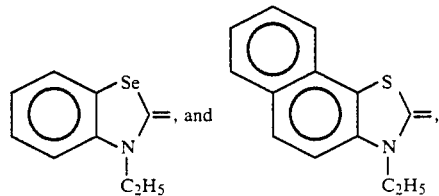
-continued
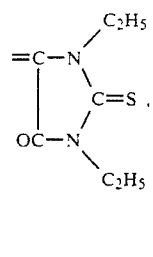 represents a ring such as
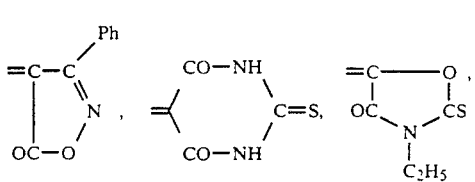
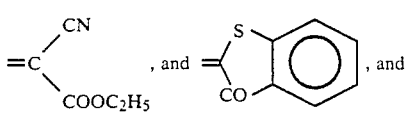
n is 1 or 2.
Typical examples of the above cyanine and merocyanine dyes are given below; however, the present invention is not restricted by these dyes.
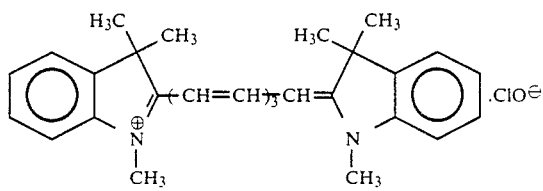 (A)
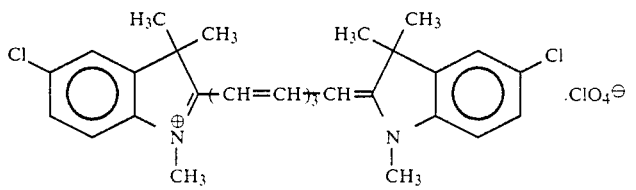 (B)
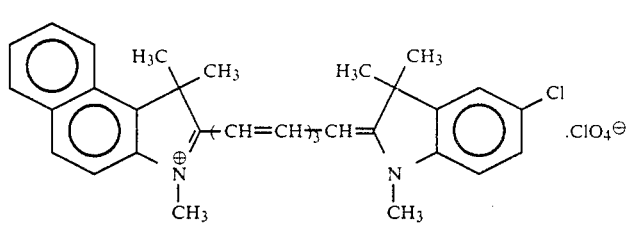 (C)
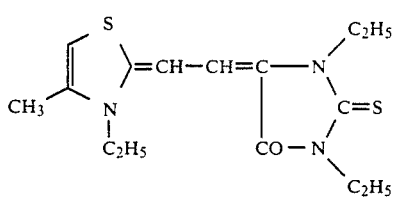 (D)
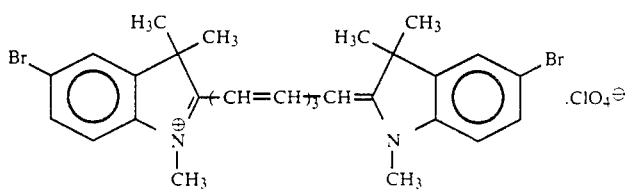 (E)

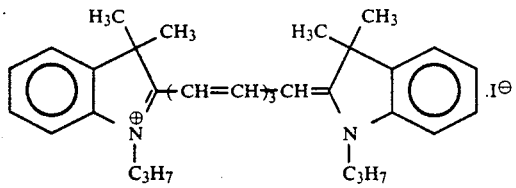

In order to improve the recording characteristics and stability, various substances can be dispersed in or laminated on the recording layer for use in the optical recording medium of the present invention. These include dyes such as a phthalocyanine dye, a tetrahydrocholine dye, a dioxadine dye, a triphenothiadine dye, a phenanthrene dye, an anthraquinone dye (indanthrene), a xanthene dye, a triphenyl methane dye, a triphenyl amine dye, and an azulene dye, as well as metals or metal compounds such as In, Sn, Te, Bi, Al, Se, Ag, $TeO_2$, SnO and Cu.

Moreover, auxiliary components such as binder agents, stabilizing agents, plasticizers, surface active agents, anti-electrification agents and dispersing agents may be incorporated into the recording layer, if necessary.

A preferable amount of the metal complex compound having formula [I] is 5 to 40 parts by weight to 100 parts by weight of the polymethyine dye contained in the recording layer.

The thickness of the recording layer ranges from 100 A to 10 μm, preferably from 200 A to 2 μm.

The recording layer can be formed by any of the known methods such as a solution-coating method, for instance, dip-coating, spray-coating, spinner-coating, blade-coating, roller-coating and curtain-coating; vacuum vapor deposition; chemical vapor deposition; and sputtering.

In the case where the solution-coating method is employed for forming the recording layer, the following solvents can be used either singly or in combination: alcohols such as isopropyl alcohol; ketones such as methyl ethyl ketone; esters such as ethyl acetate; ethers such as methyl cellosolve; halogenated alkyls such as dichloroethane and chloroform; and aromatic solvents such as toluene and xylene.

Any material can be used as a substrate on which the recording layer is formed. Examples of the material for the substrate include various plastics, glass, ceramics and metals.

As described above, the dithiolate metal complex compound having formula [I] has an absorptivity in the near-infrared region, so that it is quite useful for the optical recording medium.

The production method of the metal complex compound [I] according to the present invention simply utilizes a ligand exchange reaction between the metal complex having formula [II] or onium salt thereof and the onium salt of metal complex having formula [III], so that it is extremely advantageous from an industrial point of view.

The optical recording medium comprising the metal complex compound having formula [I] according to the present invention has improved stability in both a reproduction light and natural light, so that it can endure frequent reproduction and can be preserved for a long term. Futhermore, the recording medium can be produced by a simple process, so that production costs can be reduced.

FInally, the dithiolate metal complex compound [I] according to the present invention can be employed not only in optical recording media but also in infrared-ray-sensitive filters, selective-light-absorptive materials, heat-ray-shielding materials, and antioxidant agents.

Other features of this invention will become apparent in the course of the following description of exemplary embodiments, which are given for illustration of the invention are not intended to be limiting thereof.

SYNTHESIS EXAMPLE 1

Synthesis of (1-methyl-3,4-benzenedithiolate)-(1,2-dicyano-1,2-ethylenedithiolate)Ni(III).tetra-n-butylammonium salt (compound of complex anion 2 and complex cation 2)

(1—1) Synthesis of tetra-n-butylammonium bis(1-methyl-3,4-dithiopheno-late)Ni(III)

5 parts by weight of 3,4-dimercaptotoluene and 3.3 parts by weight of sodium hydroxide were dissolved in 40 parts by weight of methanol containing a small amount of water. To the resulting solution, 9.9 parts by weight of $NiCl_2.6H_2O$ dissolved in 25 parts by weight of methanol was added. At this stage, the mixture liberated a black precipitate.

13.4 parts by weight of tetara-n-butylammonium bromide was further added to the above mixture, and the resultant mixture was stirred for a while, followed by filtration. The filtrated black precipitate was dissolved in hot acetone, and then a small amount of hot n-butanol was added to the resulting solution. The mixture was cooled, obtaining thereby 6.9 parts by weight of the captioned compound as dark green crystals, having a melting point of 151° C. to 152° C. (152° to 153° C. in the literature).

(1-2) Synthesis of tetra-n-butylammonium bis(1,2-dicyano-1,2-ethylenedithiolate)Ni(III)

5.6 parts by weight of sodium cis-1,2-dicyano-1,2-ethylenedithiolate was dissolved in 60 parts by weight of a 1/1 (v/v) mixed solvent of water and methanol. To this solution, 3.6 parts by weight of $NiCl_2.6H_2O$ dissolved in 20 parts by weight of water was added. At this stage, the mixture turned dark red-brown in color.

10.3 parts by weight of tetra-n-butylammonium bromide dissolved in 20 parts by weight of 1/1 (v/v) mixed solvent of water and methanol was further added to the above mixture, and the resultant mixture was stirred for one hour at room temperature, followed by filtration in order to obtain precipitated orange-red crystals.

The above-obtained crystals were recrystallized from a mixed solvent of acetone and butanol, obtaining thereby 11.2 parts by weight of the captioned compound, having a melting point of 141° to 142° C. (143° to 144° C. in the literature).

(1-3) Synthesis of (1-methyl-2,4-benzenedithiolate)-(1,2-dicyano-1,2-ethylenedithiolate)Ni(III). tetra-n-butylammonium salt 0.62 parts by weight of the complex prepared in the above (1—1) was dissolved in 10 parts by weight of acetonitrile. To this solution, 0.3 parts by weight of iodine dissolved in 20 parts by weight of acetonitrile was gradually added, and the resulting mixture was stirred for five minutes at room temperature. At this stage, the mixture which had been dark green in color turned black.

0.82 parts by weight of the complex prepared in the above (1-2), dissolved in 20 parts by weight of acetonitrile was added to the above mixture, and was refluxed for five hours. The reaction mixture was filtered, and the solvent contained in the filtrate was distilled off to obtain a crude product. The product was extracted with a 1/1 (v/v) mixed solvent of ethylacetate and toluene. The extract was subjected to separation by column chromatography using silica gel (Wako Gel C-200), thereby 0.14 parts by weight of the captioned compound was obtained as green-brown crystals, having a melting point of 167° to 169° C.

The results of an elementary analysis and the absorption spectrum of the above-obtained metal complex compound are as follows. The charts of the infrared spectrum and absorption curve of the compound are shown in FIG. 1.

| | Elementary Analysis: | | | |
|---|---|---|---|---|
| | %C | %H | %N | %S |
| Calculated: | 54.45 | 7.11 | 7.05 | 21.53 |
| Found: | 53.99 | 7.32 | 7.44 | 21.14 |

Absorption Spectrum: $\lambda_{max}$892 nm.

SYNTHESIS EXAMPLE 2

Synthesis of (1,2-benzenedithiolate)-(1,2-dicyano-1,2-ethylenedithiolate)Ni(III).tetra-n-butylammonium salt (compound of complex anion 1 and complex cation 2)

(2-1) Synthesis of bis(1,2-benzenedithiolate) Ni(III).tetra-n-butylammonium 5 parts by weight of 1,2-dimercaptobenzene was dissolved in alcoholate prepared by dissolving 1.6 parts by weight of metal sodium in 50 parts by weight of methanol. To this solution, 8.3 parts by weight of $NiCl_2.6H_2O$ dissolved in 20 parts by weight of water was added. At this stage, the mixture liberated a black precipitate.

11.3 parts by weight of tetra-n-butylammonium bromide was further added to the above mixture, and the resultant mixture was stirred at 50° C. for 30 minutes, followed by filtration. The filtration black precipitate was dissolved in hot acetone, and then a small amount of hot n-butanol was added to the resulting solution. The mixture was cooled, whereby 7.2 parts by weight of the captioned compound was obtained as black crystals in the form of needles, having a melting point of 172° to 713° C.

(2—2) Synthesis of (1,2-benzenedithiolate)(1,2-dicyano-1,2-ethylenedithiolate)Ni(III).tetra-n-butylammonium salt 0.29 parts by weight of the complex prepared in the above (2-1) was dissolved in 15 parts by weight of dimethylsulfoxide. To this solution, 0.14 parts by weight of iodine dissolved in 10 parts by weight of dimethylsulfoxide was gradually added, and stirred for five minutes at room temperature. At this stage, the mixture which had been dark green in color turned black.

0.45 parts by weight of the complex prepared in the above (1-2), dissolved in 10 parts by weight of dimethylsulfoxide was added to the above mixture, and the resultant mixture was heated to between 65° and 70° C. for six hours while being stirred. The reaction mixture was filtered, and dimethylsulfoxide contained in the filtrate was distilled off, followed by extraction with a 1/1 (v/v) mixed solvent of ethylacetate and toluene, and separation of column chromatography using silica gel (Wako Gel C-200). The blue-green product thus separated was recrystallized from methanol, whereby 0.23 parts by weight of the captioned metal complex compound was obtained as blue-green crystals in the form of scales, having a melting point of 157° to 158° C.

The results of an elementary analysis and the absorption spectrum of the above-obtained metal complex compound are as follows. The charts of the infrared spectrum and absorption curve of the compound are shown in FIG. 2.

| | Elementary Analysis: | | | |
|---|---|---|---|---|
| | %C | %H | %N | %S |
| Calculated: | 53.70 | 6.93 | 7.23 | 22.05 |
| Found: | 54.01 | 6.88 | 7.16 | 21.72 |

Absorption Spectrum: $\lambda_{max}$887 nm.

Synthesis Example 3

Synthesis of (1,2,4-trichloro-5,6-benzenedithiolate)(1,2-dicyano-1,2-ethylenedithiolate)Ni(III).trihexylethylphosphonium (compound of complex anion 10 and complex cation 8)

(3-1) Synthesis of bis (1,2-dicyano-1,2-ethylenedithiolate)Ni(III).trihexylethylphosphonium 4.7 parts by weight of sodium. cis-1,2-dicyano-1,2-ethylenedithiolate was dissolved in 60 parts by weight of a 1/1 (v/v) mixed solvent of water and methanol. To this solution, 3.6 parts by weight of $NiCl_2.6H_2O$ dissolved in 20 parts by weight of water was added. At this state, the mixture turned dark red-brown.

9.8 parts by weight of trihexylethylammonium bromide dissolved in a 1/1 (v/v) mixed solvent of water and methanol was added to the above mixture, and the resultant was stirred for one hour at room temperature. The precipitated red-brown crystals were collected by filtration. The crystals thus obtained were recrystallized from methanol, obtaining thereby 5.4 parts by weight of the captioned complex compound, having a melting point of 77° to 78° C.

The above compound was subjected to an elementary analysis. The results area as follows:

| | %C | %H | %N | %P |
|---|---|---|---|---|
| Calculated: | 59.43 | 9.14 | 5.78 | 6.39 |
| Found: | 59.25 | 8.99 | 5.70 | 6.0 |

(3-2) Synthesis of
(1,2,4-trichloro-5,6-benzenedithiolate)-(1,2-dicyano-1,2-ethylenedithiolate)Ni(III).trihexylethylphosphonium 1.0 parts by weight of bis(1,2,4-trichloro-5,6-benzenedithiolate)Ni(III).tetra-n-butylammonium was dissolved in 30 parts by weight of 1,2-dichloroethane. To this solution, 0.26 parts by weight of iodine suspended in 10 parts by weight of 1,2-dichloroethane was added, and stirred for 10 minutes at room temperature. At this stage, the mixture which had been dark green in color turned black.

1.2 parts by weight of the complex prepared in (1-2) was added to the above mixture, and the resultant was heated to between 80° and 85° C. for 6 hours while being stirred. The reaction mixture was filtered, and 1,2-dichloroethane contained in the filtrate was distilled off, followed by extraction with 150 parts by weight of toluene. 0.5 part by weight of tri-n-hexyl-ethylphosphonium bromide dissolved in 50 parts by weight of water was added to the extract, and the resultant was stirred for one hour at room temperature so as to proceed a cation exchange reaction. After the reaction was completed, the toluene layer was separated from the reaction system, and toluene was distilled off from the toluene layer, followed by extraction with a 1/1 (v/v) mixed solvent of ethylacetate and toluene. The extract was subjected to separation by column chromatography using silica gel (Wako Gel C-200), and a solvent was distilled off in order to obtain a dark green crude product. The product thus obtained was recrystallized from a mixed solvent of acetone and n-butanol, whereby 0.38 parts by weight of the captioned metal complex compound was obtained as dark green crystals, having a melting point of 59° to 61° C.

Figures 1, 3:
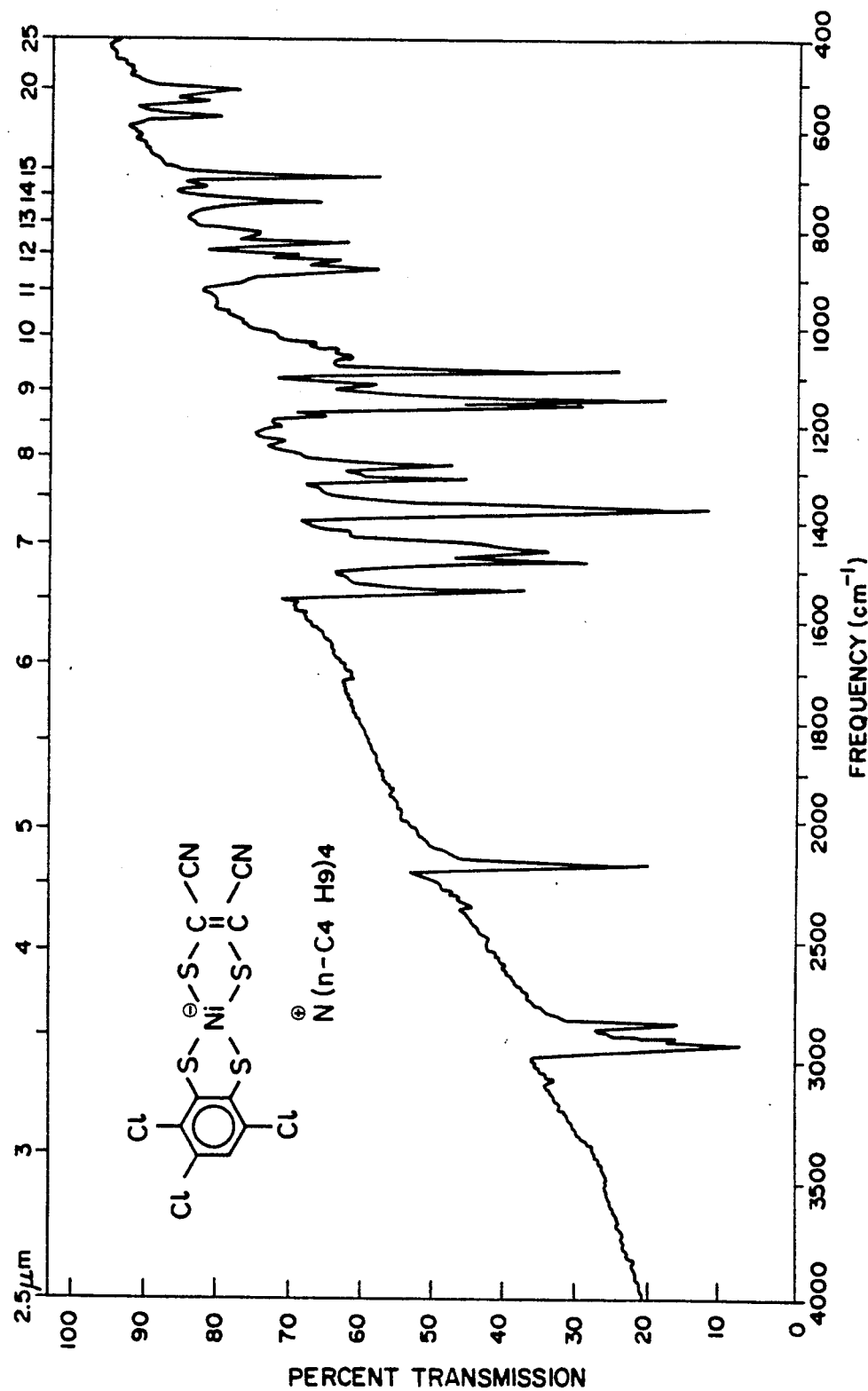
Figures 2, 3:
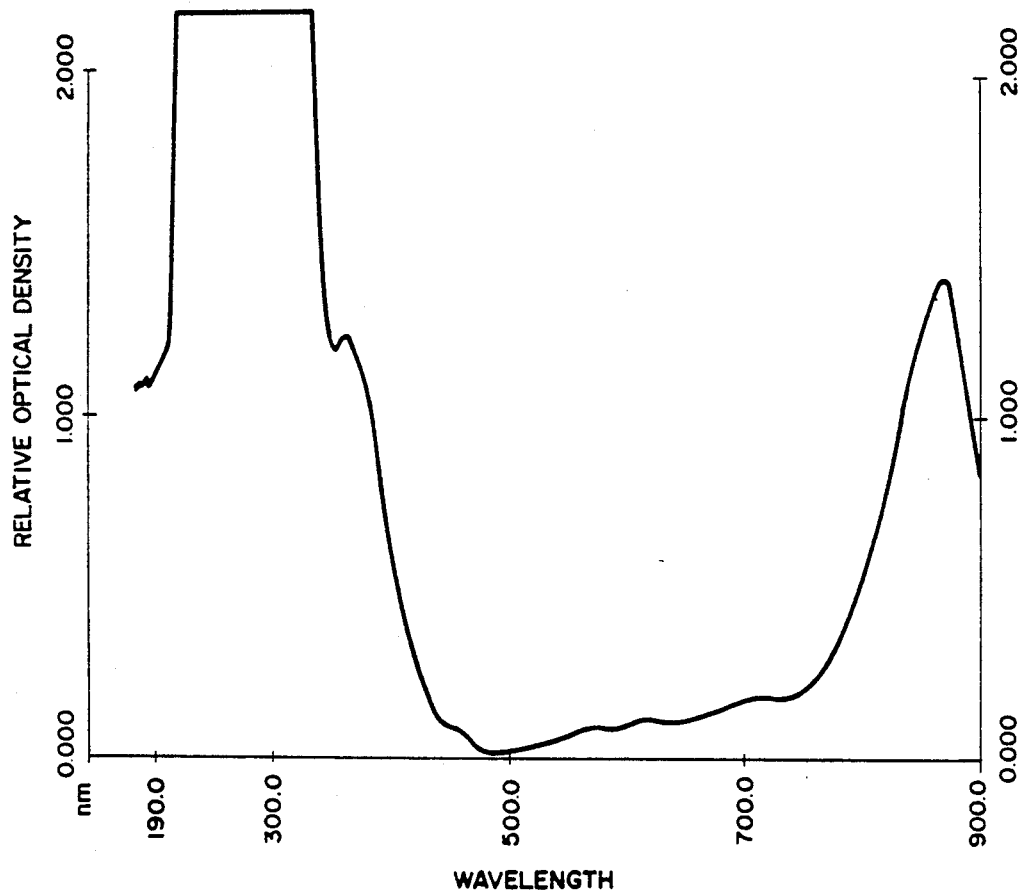

The results of an elementary analysis and the absorption spectrum of the above-obtained metal complex compound are as follows. The charts of the infrared spectrum and absorption curve of the compound are shown in FIG. 3.

|  | Elementary Analysis: | | | |
| --- | --- | --- | --- | --- |
|  | %C | %H | %N | %P |
| Calculated: | 47.54 | 5.98 | 3.70 | 4.09 |
| Found: | 47.28 | 6.06 | 3.54 | 3.87 |

Absorption Spectrum: $\lambda_{max}$ 883 nm.

EXAMPLE 1

A mixture of (i) 100 parts by weight of cyanine dye (A) (Trademark NK-2421, made by Japanese Research Institute for Photosensitizing Dyes Co., Ltd.), which is one of the previously mentioned examples of cyanine dyes and merocyanine dyes (A) through (F), and (ii) 15 parts by weight of (1,2-benzenedithiolate)-(1,2-dicyano-1,2-ethylenedithiolate)Ni(III).tetra-n-butylammonium salt prepared in Synthesis Example 2 was dissolved in an 8/2 (v/v) mixed solvent of methanol and 2,2'-dichloroethane in an amount of 0.6 wt. % based on the mixed solvent. The resulting solution was applied to a glass substrate and dried to provide a recording layer having a thickness of 600 Å, whereby a recording medium No. 1 according to the present invention was prepared.

A light of 54,000 lux was applied to the recording medium by using a tungsten lamp of 500 W, and then the extinction speed of the absorption peak of the dye contained in the recording layer was measured. The above extinction speed was compared with (i) that of the recording medium whose recording layer does not contain the above Ni complex, and (ii) that of the recording medium whose recording layer contains bis(1,2,4-tirchloro-5,6-benzenedithiolate)Ni(III).tetra-n-butylammonium instead of the above Ni complex. As a result, the extinction speed of the recording medium No. 1 was 0.1 of that of the above recording medium (i), and 0.5 of that of the above recording medium (ii).

Furthermore, the stability to the reproduction light was confirmed. As a result, the recording medium No. 1 was at least 20 times more stable than the recording medium (i), and at least 2 times more stable than the recording medium (ii).

EXAMPLE 2

Example 1 was repeated except that (1,2-benzenedithiolate)-(1,2-dicyano-1,2-ethylenedithiolate)Ni(III).tetra-n-butylammonium salt prepared in Synthesis Example 2 was replaced by (1-methyl-3,4-benzenedithiolate)-1,2-dicyano-1,2-ethylenedithiolate)Ni(III).tetra-n-butylammonium salt prepared in Synthesis Example 1, whereby a recording medium No. 2 according to the present invention was prepared.

The above-prepared recording medium was evaluated in the same manner as in Example 1. As a result, the extinction speed of the absorption peak of the dye contained in the recording layer of the recording medium No. 2 was 0.08 of that of the above-described recording medium (i), and 0.44 of that of the above-described recording medium (ii). With respect to the stability in the reproduction light, the recording medium No. 2 was 22 times more stable than the recording medium (i), and at least 2.5 times more stable than the recording medium (ii).

EXAMPLE 3

Example 1 was repeated except that (1,2-benzenedithiolate)-(1,2-dicyano-1,2-ethylenedithiolate)Ni(III).tetra-n-butylammonium salt prepared in Synthesis Example 2 was replaced by (1,2,4-trichloro-5,6-benzenedithiolate)-(1,2-dicyano-1,2-ethylenedithiolate)Ni-(III).-trihexyl-ethylphosphonium prepared in Synthesis Example 3, whereby a recording medium No. 3 according to the present invention was prepared.

The above-prepared recording medium was evaluated in the same manner as in Example 1. As a result, the extinction speed of the absorption peak of the dye contained in the recording layer of the recording medium No. 3 was 0.07 of that of the above-described recording medium (i), and 0.40 of that of the above-described recording medium (ii). With respect to the stability in the reproduction light, the recording medium (i), and at least 2.5 times more stable than the recording medium (ii).

EXAMPLE 4

A spiral groove having a pitch of 1.6 μm, a depth of 2000 Å, and a half width of 0.4 μm was formed on an acrylic photopolymer layer, 50 μm in thickness, provided on a polymethylmethacrylate (PMMA) disk having a thickness of 1.2 mm and a diameter of 130 mm.

A mixture of 100 parts by weight of the cyanine dye (E) and 15 parts by weight of (1,2,4-trichloro-5,6-benzenedithiolate)-(1,2-dicyano-1,2-ethylenedithiolate)-Ni(III).tetra-n-butylammonium salt (a compound of complex anion 10 and complex cation 2) was dissolved in 1,2-dichloroethane in an amount of 0.8 wt. % based on the 1,2-dichloroethane. The resulting solution was spin-coated onto the above prepared substrate, and dried to provide a recording layer having a thickness of about 800 Å, whereby a recording medium No. 4 according to the present invention was prepared.

In order to evaluate the recording characteristics of the above recording medium, information was recorded in the recording medium, from the substrate-side, by using a semiconductor laser beam having a wavelength of 790 nm and a beam diameter of 1.6 μm under the conditions of a recording frequency of 1.25 MHz, a line speed of 2.1 m/sec, and a recording power of 2.5 mW. By using the same semiconductor laser beam, the recorded area was reproduced with an intensity of 0.2 mW. At this time, the reflected light was detected, and subjected to a spectrum analysis using a scanning filter of 30 kHz to determine the initial C/N ratio.

As an acceleration test for repeated-reproduction-stability, a reproduction light of 0.25 mW was applied to the same address 1,000,000 times, and changes of the signal output at the non-recorded area and the signal amplitude at the recorded area were measured. the results are shown in Table 1.

EXAMPLE 5

Example 4 was repeated except that (1,2,4-trichloro-5,6-benzenedithiolate)-(1,2-dicyano-1,2-ethylenedithiolate)Ni(III).tetra-n-butylammonium salt used in Example 4 was replaced by (1-methyl-3,4-benzenedithiolate)-(1,2-dicyano-1,2-ethylenedithiolate)Ni(III).tetra-n-butylammonium salt prepared in Synthesis Example 1, whereby a recording medium No. 5 according to the present invention was prepared.

The above recording medium was evaluated in the same manner as in Example 4. The results are shown in Table 1.

EXAMPLE 6

A polycarbonate substrate was prepared by injection molding using a stamper having the same groove-pattern as the one provided on the substrate in Example 4.

A mixture of 100 parts by weight of the cyanine dye (F) and 15 parts by weight of (1,2,4-trichloro-5,6-benzenedithiolate)-(1,2-dicyano-1,2-ethylenedithiolate)-Ni(III).tetra-n-butylphosphonium (a compound of complex anion 10 and complex cation 7) was dissolved in an 85/15 (weight basis) mixed solvent of methanol and 1,2-dichloroethane in an amount of 0.7 wt. % based on the mixed solvent. The resulting solution was spin-coated onto the above substrate, and dried to provide a recording layer, whereby a recording medium No. 6 according to the present invention was prepared.

The above recording medium was evaluated in the same manner as in Example 4. The results are shown in Table 1.

EXAMPLE 7

Example 6 was repeated except that (1,2,4-trichloro-5,6-benzenedithiolate)-(1,2-dicyano-1,2-ethylenedithiolate)Ni(III).tetra-n-butylphosphonium was replaced by (1,2-benzenedithiolate)-(1,2-dicyano-1,2-ethylenedithiolate)Ni(III).tetra-n-butylammonium salt prepared in Synthesis Example 2, whereby a recording medium No. 7 according to the present invention was prepared.

The above recording medium was evaluated in the same manner as in Example 4. The results are shown in Table 1.

EXAMPLE 8

Example 6 was repeated except that (1,2,4-trichloro-5,6-benzenedithiolate)-(1,2-dicyano-1,2-ethylenedithiolate)Ni(III).tetra-n-butylphosphonium was replaced by (1,4-dichloro-5,6-benzenedithiolate)-(1,2-dicyano-1,2-ethylenedithiolate)Ni(III).tetra-n-butylammonium salt (a compound of complex anion 9 and complex cation 2), whereby a recording medium No. 8 according to the present invention was prepared.

The above recording medium was evaluated in the same manner as in Example 4. The results are shown in Table 1.

COMPARATIVE EXAMPLE 1

Example 4 was repeated without using (1,2,4-trichloro-5,6-benzenedithiolate)-(1,2-dicyano-1,2-ethylenedithiolate)Ni(III).tetra-n-butylammonium salt, whereby a comparative recording medium No. 1 was prepared.

The above recording medium was evaluated in the same manner as in Example 4. The results are shown in Table 1.

COMPARATIVE EXAMPLE 2

Example 6 was repeated without using (1,2,4-trichloro-5,6-benzenedithiolate)-(1,2-dicyano-1,2-ethylenedithiolate)Ni(III).tetra-n-butylphosphonium, whereby a comparative recording medium No. 2 was prepared.

the above recording medium was evaluated in the same manner as in Example 4. The results are shown in Table 1.

Table 1

| Recording Medium | Initial C/N Ratio (dB) | Change of Signal after 1,000,000 Time Reproduction | |
|---|---|---|---|
| | | Signal Output at Non-recorded Area (%) | Signal Amplitude at Recorded Area (%) |
| No. 4 | 54 | −6 | −8 |
| No. 5 | 53 | −10 | −14 |
| No. 6 | 54 | −7 | −9 |
| No. 7 | 54 | −14 | −17 |
| No. 8 | 53 | −8 | −12 |
| Comp. No. 1 | 55 | −51 | −60 |
| Comp. No. 2 | 54 | −60.2 | −72 |

The above data clearly demonstrate that the optical information recording media according to the present invention are highly stable in the reproduction light.

What is claimed is:

1. A dithiolate metal complex compound consisting of an anion and a counter cation, having formula:

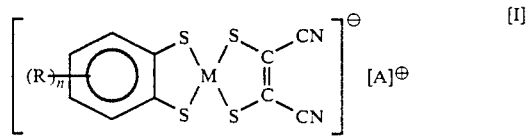

wherein
each R individually represents an alkyl group having 1 to 6 carbon atoms, a halogen, a halogenated alkyl group having a 1 to 6 carbon atoms, an anion group which may be substituted with 1 or 2 alkyl groups each having independently 1 to 4 carbon atoms, or a trifluoromethyl group, M represents a transition metal selected from the group consisting of Ni, Pd, Pt, Co, Cu and Mn, n is an integer of 0 to 4, and A represents the counter cation of the complex compound.

2. A method of producing a dithiolate metal complex compound consisting of an anion and a counter cation, having formula:

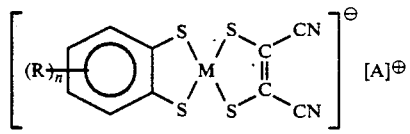 [I]

wherein
each R individually represents an alkyl group having 1 to 6 carbon atoms, a halogen, a halogenated alkyl group having 1 to 6 carbon atoms, an amino group which may be substituted with 1 or 2 alkyl groups each having independently 1 to 4 carbon atoms, or a trifluoromethyl group, M represents a transition metal selected from the group consisting of Ni, Pd, Pt, Co, Cu and Mn, n is an integer of 0 to 4, and A represents the counter cation of the complex compound, comprising the step of:

reacting (a) a neutral dithiolate metal complex having formula or an onium salt of the monoanion thereof:

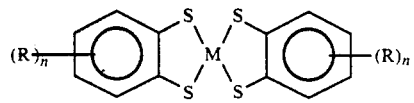 [II]

wherein
each R individually represents an alkyl group having 1 to 6 carbon atoms, a halogen, a halogenated alkyl group having 1 to 6 carbon atoms, an amino group which may be substituted with 1 or 2 alkyl groups each having independently 1 to 4 carbon atoms, or a trifluoromethyl group, M represents a transition metal selected from the group consisting of Ni, Pd, Pt, Co, Cu and Mn, and n is an integer of 0 to 4, with (b) bis-(onium) salt of a dicyanoethylenedithiolate metal complex having formula:

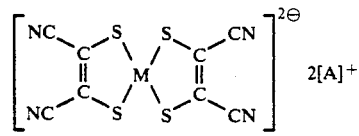 [III]

wherein
M represents a transition metal selected from the group consisting of Ni, Pd, Pt, Co, Cu and Mn, and A represents the counter cation of the complex compound.

3. The dithiolate metal complex compound as claimed in claim 1, wherein the anion of said dithiolate metal complex compound has the formula of

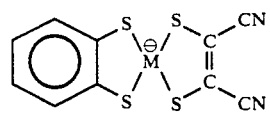

wherein M represents a transition metal selected from the group consisting of Ni, Pd, Pt, Co, Cu and Mn.

4. The dithiolate metal complex compound as claimed in claim 1, wherein the anion of said dithiolate metal complex compound has the formula of

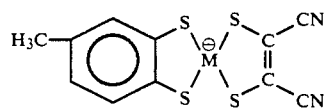

wherein M represents a transition metal selected from the group consisting of Ni, Pd, Pt, Co, Cu and Mn.

5. The dithiolate metal complex compound as claimed in claim 1, wherein the anion of said dithiolate metal complex compound has the formula of

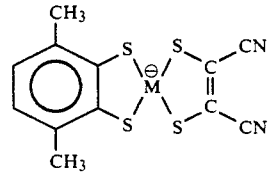

wherein M represents a transition metal selected from the group consisting of Ni, Pd, Pt, Co, Cu and Mn.

6. The dithiolate metal complex compound as claimed in claim 1, wherein the anion of said dithiolate metal complex compound has the formula of

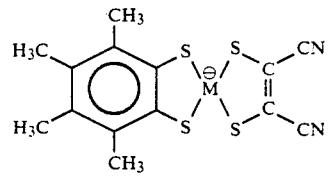

wherein M represents a transition metal selected from the group consisting of Ni, Pd, Pt, Co, Cu and Mn.

7. The dithiolate metal complex compound as claimed in claim 1, wherein the anion of said dithiolate metal complex compound has the formula of

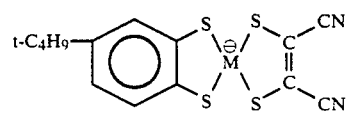

wherein M represents a transition metal selected from the group consisting of Ni, Pd, Pt, Co, Cu and Mn.

8. The dithiolate metal complex compound as claimed in claim 1, wherein the anion of said dithiolate metal complex compound has the formula of

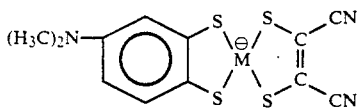

wherein M represents a transition metal selected from the group consisting of Ni, Pd, Pt, Co, Cu and Mn.

9. The dithiolate metal complex compound as claimed in claim 1, wherein the anion of said dithiolate metal complex compound has the formula of

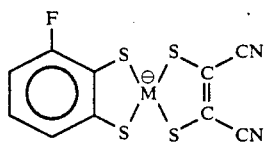

wherein M represents a transition metal selected from the group consisting of Ni, Pd, Pt, Co, Cu and Mn.

10. The dithiolate metal complex compound as claimed in claim 1, wherein the anion of said dithiolate metal complex compound has the formula of

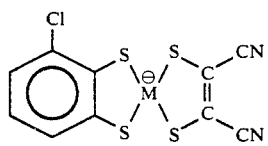

wherein M represents a transition metal selected from the group consisting of Ni, Pd, Pt, Co, Cu and Mn.

11. The dithiolate metal complex compound as claimed in claim 1, wherein the anion of said dithiolate metal complex compound has the formula of

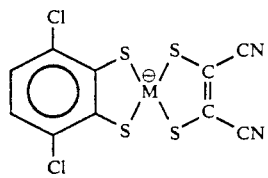

wherein M represents a transition metal selected from the group consisting of Ni, Pd, Pt, Co, Cu and Mn.

12. The dithiolate metal complex compound as claimed in claim 1, wherein the anion of said dithiolate metal complex compound has the formula of

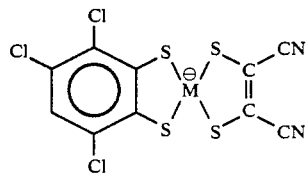

wherein M represents a transition metal selected from the group consisting of Ni, Pd, Pt, Co, Cu and Mn.

13. The dithiolate metal complex compound as claimed in claim 1, wherein the anion of said dithiolate metal complex compound has the formula of

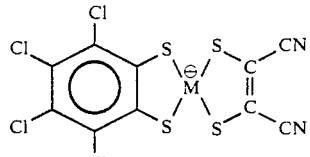

wherein M represents a transition metal selected from the group consisting of Ni, Pd, Pt, Co, Cu and Mn.

14. The dithiolate metal complex compound as claimed in claim 1, wherein the anion of said dithiolate metal complex compound has the formula of

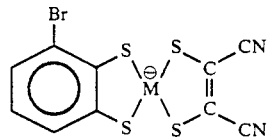

wherein M represents a transition metal selected from the group consisting of Ni, Pd, Pt, Co, Cu and Mn.

15. The dithiolate metal complex compound as claimed in claim 1, wherein the anion of said dithiolate metal complex compound has the formula of

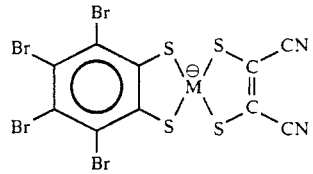

wherein M represents a transition metal selected from the group consisting of Ni, Pd, Pt, Co, Cu and Mn.

16. The dithiolate metal complex compound as claimed in claim 1, wherein the anion of said dithiolate metal complex compound has the formula of

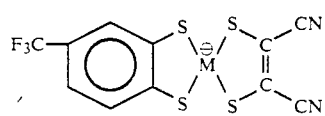

wherein M represents a transition metal selected from the group consisting of Ni, Pd, Pt, Co, Cu and Mn.

17. The dithiolate metal complex compound as claimed in claim 3, wherein said anion is (1,2-benzenedithiolate)-(1,2-dicyano-1,2-ethylenedithiolate)Ni(III).

18. The dithiolate metal complex compound as claimed in claim 4, wherein said anion is (1-methyl-3,4-benzenedithiolate)-(1,2-dicyano-1,2-ethylenedithiolate)-Ni(III).

19. The dithiolate metal complex compound as claimed in claim 5, wherein said anion is (1,4-dimethyl-2,3-benzenedithiolate)-(1,2-dicyano-1,2-ethylenedithiolate)Ni(III).

20. The dithiolate metal complex compound as claimed in claim 6, wherein said anion is (1,2,3,4-tetramethyl-5,6-benzenedithiolate)-(1,2-dicyano-1,2-ethylenedithiolate)Ni(III).

21. The dithiolate metal complex compound as claimed in claim 7, wherein said anion is (1-t-butyl-3,4-benzenedithiolate)-(1,2-dicyano-1,2-ethylenedithiolate)-Ni(III).

22. The dithiolate metal complex compound as claimed in claim 8, wherein said anion is (1-dimethylamino-3,4-benzenedithiolate)-(1,2-dicyano-1,2-ethylenedithiolate)Ni(III).

23. The dithiolate metal complex compound as claimed in claim 9, wherein said anion is (1-fluoro-2,3-benzenedithiolate)-(1,2-dicyano-1,2-ethylenedithiolate)-Ni(III).

24. The dithiolate metal complex compound as claimed in claim 10, wherein said anion is (1-chloro-2,3-benzenedithiolate)-(1,2-dicyano-1,2-ethylenedithiolate)-Ni(III).

25. The dithiolate metal complex compound as claimed in claim 11, wherein said anion is (1,4-dichloro-5,6-benzenedithiolate)-(1,2-dicyano-1,2-ethylenedithiolate)Ni(III).

26. The dithiolate metal complex compound as claimed in claim 12, wherein said anion is (1,2,4-trichloro-5,6-benzenedithiolate)-(1,2-dicyano-1,2-ethylenedithiolate)Ni(III).

27. The dithiolate metal complex compound as claimed in claim 13, wherein said anion is (1,2,3,4-tetrachloro-5,6-benzenedithiolate)-(1,2-dicyano-1,2-ethylenedithiolate)Ni(III).

28. The dithiolate metal complex compound as claimed in claim 14, wherein said anion is (1-bromo-2,3-benzenedithiolate)-(1,2-dicyano-1,2-ethylenedithiolate)-Ni(III).

29. The dithiolate metal complex compound as claimed in claim 15, wherein said anion is (1,2,3,4-tetrabromo-5,6-benzenedithiolate)-(1,2-dicyano-1,2-ethylenedithiolate)Ni(III).

30. The dithiolate metal complex compound as claimed in claim 16, wherein said anion is (1-trifluoromethyl-3,4-benzenedithiolate)-(1,2-dicyano-1,2-ethylenedithiolate)Ni(III).

31. The dithiolate metal complex compound as claimed in claim 1, wherein the counter cation of said dithiolate metal complex is selected from the group consisting of:
tetraethylammonium cation,
tetra-n-butylammonium cation,
benzyl-tributylammonium cation,
N-laurylpyrridinium cation,
N-benzylpicolinium cation,
trimethyl-hexadecaneammonium cation,
tetra-n-butylphosphonium cation,
trihexylethylphosphonium cation, and
tetraoctylphosphonium cation.

32. An optical information recording medium comprising:
a substrate, and
a recording layer formed on said substrate, comprising a polymethine dye and a dithiolate metal complex compound having formula:

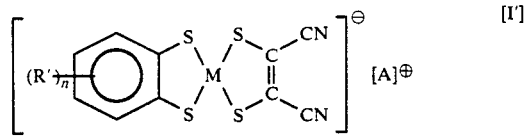

wherein
each R' individually represents an alkyl group having 1 to 6 carbon atoms, a halogen, a halogenated alkyl group having 1 to 6 carbon atoms, an amino group which may be substituted with 1 or 2 alkyl groups each having independently 1 to 4 carbon atoms, a cyano group, a nitro group, or a trifluoromethyl group,
M represents a transition metal selected from the group consisting of Ni, Pd, Pt, Co, Cu and Mn,
n is an integer of 0 to 4, and
A represents the counter cation of the complex compound.

33. The optical information recording medium as claimed in claim 32, wherein the amount of said dithiolate metal complex compound is 5 to 40 parts by weight to 100 parts by weight of said polymethine dye.

34. The optical information recording medium as claimed in claim 32, wherein said polymethine dye is selected from the group consisting of cyanine dyes, merocyanine dyes, cronconium dyes, pyrylium dyes, azulenium dyes and squalyrium dyes.

35. The optical information recording medium as claimed in claim 32, wherein said recording layer further comprises a dye selected from the group consisting of a phthalocyanine dye, a tetrahydrocholine dye, a dioxadine dye, a triphenothiadine dye, a phenanthrene dye, an anthraquinone dye (indanthrene), a xanthene dye, a triphenyl methane dye, a triphenyl amine dye, and an azulene dye.

36. The optical information recording medium as claimed in claim 32, wherein said recording layer further comprises a metal selected from the group consisting of In, Sn, Te, Bi, Al, Se, Ag and Cu.

37. The optical information recording medium as claimed in claim 32, wherein said recording layer further comprises a metal compound selected from the group consisting of teO$_2$ and SnO.

38. The optical information recording medium as claimed in claim 32, further comprising an undercoat layer interposed between said substrate and said recording layer.

39. The optical information recording medium as claimed in claim 32, further comprising a protective player on said recording layer.

40. The optical recording medium as claimed in claim 32, wherein said recording layer has a thickness of 100 A to 10 μm.

* * * * *